United States Patent [19]

Banko

[11] 4,368,734
[45] Jan. 18, 1983

[54] SURGICAL INSTRUMENT

[75] Inventor: Anton Banko, Bronx, N.Y.

[73] Assignee: Surgical Design Corp., Long Island City, N.Y.

[21] Appl. No.: 872,944

[22] Filed: Jan. 27, 1978

[51] Int. Cl.³ .............................................. A61B 17/32
[52] U.S. Cl. ................................................... 128/305
[58] Field of Search .............................. 128/305, 276

[56] References Cited

U.S. PATENT DOCUMENTS

| 1,493,240 | 5/1924 | Bohn | 128/305 |
|---|---|---|---|
| 3,732,858 | 5/1973 | Banko | 128/305 |
| 3,805,787 | 4/1974 | Banko | 128/303 |
| 3,815,604 | 6/1974 | O'Malley | 128/305 |
| 3,844,272 | 10/1974 | Banko | 128/305 |
| 3,902,498 | 9/1975 | Niederer | 128/305 |
| 3,937,222 | 2/1976 | Banko | 128/305 |
| 3,945,375 | 3/1976 | Banko | 128/305 |
| 4,099,529 | 7/1978 | Peyman | 128/305 |

Primary Examiner—Richard J. Johnson
Attorney, Agent, or Firm—Darby & Darby

[57] ABSTRACT

A surgical instrument for removing objects from the body of a human or animal in vitro in which a hook type implement is utilized to grasp a portion of the object to be removed and to bring it into a relationship with a cutting surface of another portion of the instrument to provide a combined crushing and cutting action. In the preferred embodiment of the invention, suction pressure and irrigation fluid is supplied through the instrument with the cut material being removed from the area by the suction pressure.

20 Claims, 18 Drawing Figures

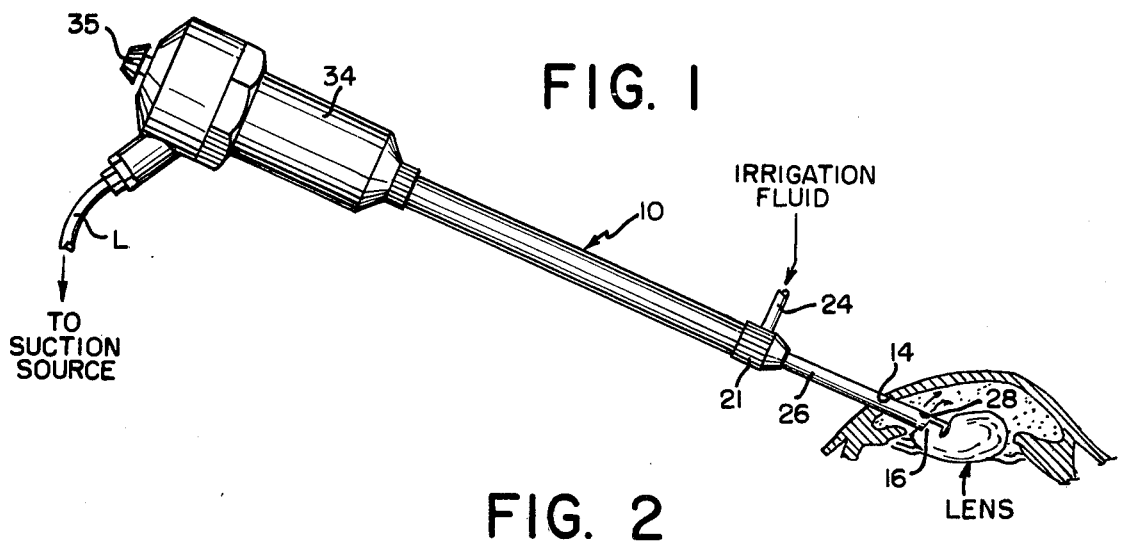
FIG. 1
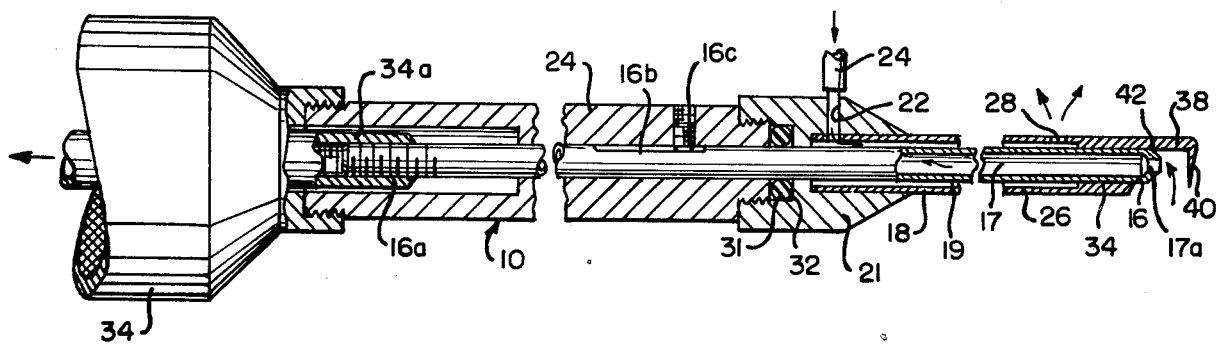
FIG. 2
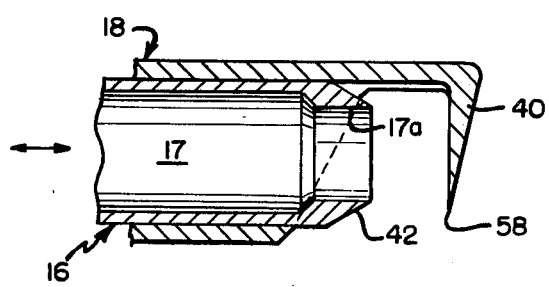
FIG. 3A
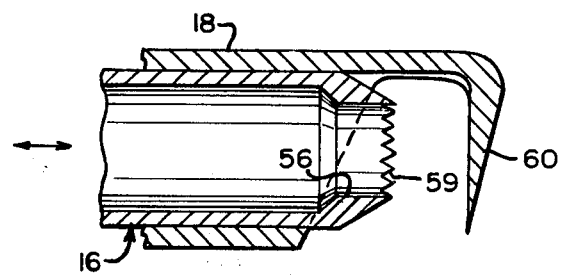
FIG. 4A
FIG. 3B
FIG. 4B
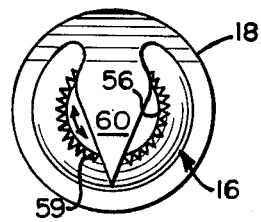

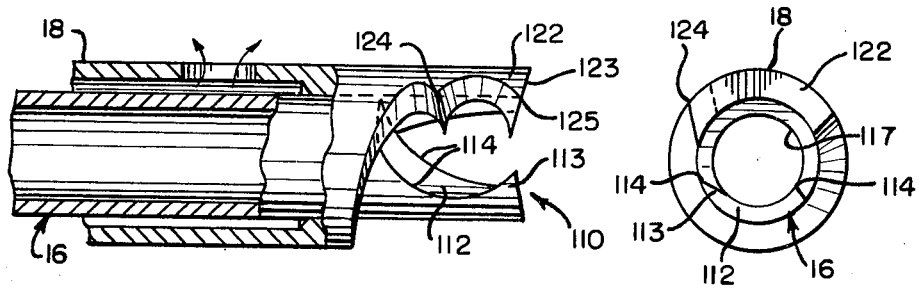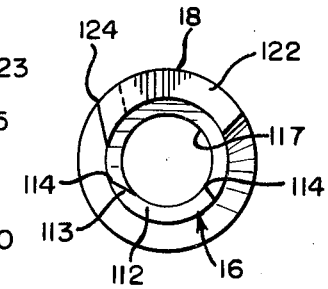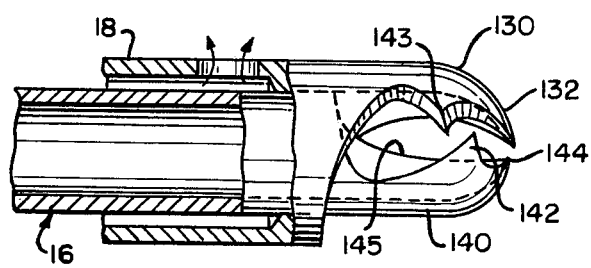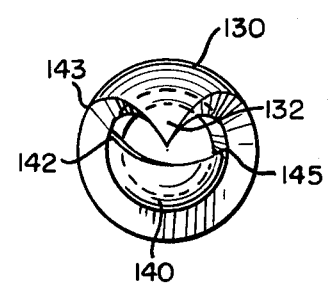

SURGICAL INSTRUMENT

Certain surgical applications exist where an object is to be removed from the body of a human or animal in vitro. In a typical case, an incision is made in the body and a surgical instrument is inserted through the incision to remove the material. One application of this type exists in the removal of diseased lenses, or cataracts, from the eye of a human being. Several types of instruments heretofore have been used for this particular application of material removal, for example, those shown in my U.S. Pat. No. 3,805,787 issued Apr. 23, 1974, and my U.S. Pat. No. 3,732,858 issued May 15, 1973, both of which are assigned to the assignee of the subject application.

In some cases, where the object to be removed is relatively hard, such as a cataract in an advanced stage, various techniques have been utilized to try to remove it. Typical of these techniques are the use of ultrasonic energy applied by a probe to the object to emulsify the material, that is, to more or less reduce it to a semi-solid or liquid state. In many cases ultrasonic energy is not effective to remove material from a relatively hard object. This is due to several factors such as the necessity of maintaining a safe level of energy in the area surrounding the object, with this level being lower than that needed to remove the material. In addition, in some cases ultrasonic energy is simply not capable of performing the required task. For example, in the case of operating in the eye, ultrasonic energy cannot readily break, or emulsify, the bag around the lens nor can it break up the posterior capsule.

Difficulties also exist with certain types of mechanical cutters in removing material from hard objects. For example, in a case where the nucleus of a cataract becomes very hard it will not easily accommodate itself to a round-shaped cutter of the type disclosed in the aforesaid U.S. Pat. No. 3,732,858. Also, it is difficult to hold hard material being cut in the proper relationship to the cutter. Where suction pressure is used to draw the material into an opening into a cutting relationship with the cutter, it sometimes happens that hard material of a specific shape will not accommodate itself to the suction opening to permit the material to be severed to be drawn into the opening by the evacuation pressure where it can be severed.

The present invention relates to a surgical instrument of a mechanical type for removing in vitro objects of relatively hard material, such as cataracts and the nucleii of cataracts, through an incision made in the body of a human or animal. According to the invention, the instrument operates with a scooping type action to grasp and hold the material to be removed and a crushing type action. The instrument is also capable of cutting the material so that the material is separated from the object by a combined crushing and cutting action and evacuated by friction pressure.

The preferred embodiment of the instrument comprises first and second tubular members mounted concentrically with each other. The inner member has a cutting edge formed on its front portion and the outer member has a scoop, or rake. The two members are movable longitudinally and/or angularly with respect to each other so that there is relative motion between the scoop and the cutting edge. In operation of a preferred embodiment of the invention, the member having the scoop is extended with respect to the cutter and the material to be severed from the object is held therebetween. The two members are then moved toward each other to cause the material between the inner face of the scoop and the cutter to be crushed and cut and thereby severed from the object.

In operation of other embodiments, the inner and outer members are provided with jaws which are rotatable relative to each other. The material to be severed is captured between the jaws and severed.

In the preferred embodiment of the invention, suction pressure is applied through a passage in the inner member to draw the cut material through the instrument for removal from the operating field. Irrigation fluid is also preferably supplied through a passage between the two members to maintain a predetermined pressure within the object being operated upon or for other purposes.

It is therefore an object of the invention to provide a surgical instrument having a combined crushing and cutting action.

Another object is to provide a surgical instrument having two members which are moved longitudinally with respect to each other, one of the members grasping the material to bring it into contact with another member which cuts the material.

A further object is to provide a surgical instrument capable of removing material by a combined crushing and cutting action wherein two members are used, one of which bring the material to be removed into an active relationship with respect to the other and the crushing and cutting taking place between the two.

Yet a further object is to provide a surgical instrument having two members which are rotatable relative to each other each having a jaw on its end for crushing material trapped between the jaws.

An additional object is to provide a surgical instrument which has a scoop to draw the material to be severed from an object against a cutting surface.

Other objects and advantages of the present invention will become more apparent upon reference to the following specification and annexed drawings in which:

FIG. 1 is a plain view of the instrument of the present invention shown in place for operating in an eye;

FIG. 2 is a plain view, partly in cross-section, of a preferred embodiment of the instrument;

Figure 5A:
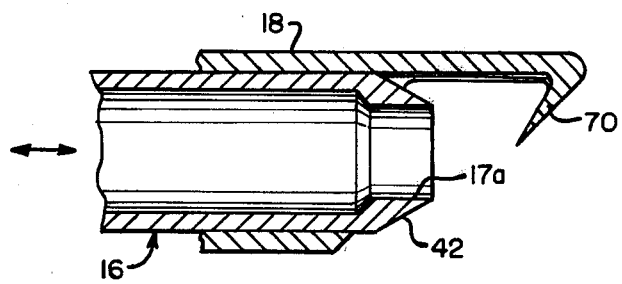

FIGS. 3A–3B through 8A–8B respectively, show fragmentary side views in cross-section, and a front view of different types of active ends of the instrument; and FIGS. 9A–9B and 10A–10B are side fragmentary views in cross-section and front views of instruments with jaw-type crushers.

Referring to FIGS. 1 and 2, the instrument 10 of the invention is shown in use operating in an eye. An incision 14 is made in the eye and the active end of the instrument passes through the incision to operate on and remove material from a lens in the eye. This lens can be considered as being relatively hard and also somewhat crunchy, like the crust of a loaf of hard bread. The interior of the eye constitutes the operating field.

The active end of the instrument which is inserted through the incision includes an inner tubular member 16 and an outer tubular member 18. Two members are mounted concentrically to permit both longitudinal and rotational motion with respect to each other. The inner member 16 is hollow through its length to provide a passage 17 terminating in an open end 17a. Passage 17 is used, as is described below, to supply suction pressure to the operating field. The two members 16, 18 are spaced from each other along a portion of their lengths to form a passage 19 which is used to supply an irrigation fluid to the operating field.

The rear end of the outer member 18 is held in a threaded cap 21 which has an opening 22 formed therein and an inlet conduit 24 fastened in the opening. The opening 22 communicates with the passage 19 and an exit port 28 is provided in member 18 so that fluid in passage 19 can leave the instrument. Cap 21 is threaded onto a sleeve 24 through which the inner member 16 passes. Irrigation fluid, such as sterile or saline solution, or any other suitable fluid, is provided through the conduit 24 from a source (not shown) into passage 19 to exit through the opening 28 into the operating area. An O ring 31 is placed in a recess 32 in the cap 21 to prevent the irrigation fluid from leaking out of the instrument. The pressure of the irrigation fluid can be adjusted to prevent the operating field, here the eye, from collapsing.

A guide, or bearing, surface 34 is formed on the inner face of the front end of the outer member forward of the exit port 28. Surface 34 terminates the passage 19 and acts as a bearing as the two members 16 and 18 are moved relative to each other. The two members are movable longitudinally with respect to each other. As shown in FIG. 1, a motor 34 is threadably mounted on the sleeve 24. Motor 34 has a slow rotational speed or, preferably, its speed can be controlled by any suitable motor control device (not shown). The inner shaft 34a of the motor is hollow and is tapped at its end within sleeve 24 to accept the threaded end 16a of inner member 16. An elongated groove 16b is provided in the member 16 and a set screw 16c is threaded into sleeve 24 and rides in the groove. A knob 35 extends outwardly from the motor housing 34 and is connected to shaft 34a to permit manual rotation of the shaft. When the motor 34 is energized, threaded shaft 34a will rotate. Since inner member 16 is held against rotating by set screw 16c, the net result will be that member 16 will move longitudinally with respect to the member 18.

The outer member 18 has a thickened front end portion 38 which terminates in a scoop, or hook, implement 40 extending over the front end of the instrument.

The front end of inner member 16 surrounding the opening 17a has a cutting surface 42 which is described in greater detail below.

A suction line L, connected to a motor driven suction pump or a syringe (not shown), is coupled to the hollow motor shaft 34 and, in turn, to the passage 17. This provides suction pressure at the open end 17a of the inner member 16. This can be done either manually or by a motor.

FIGS. 3A and 3B show the details of the active front portion of the instrument of a preferred embodiment of the invention. In this embodiment, the front end of the inner member 16 is circular in shape and is formed with a sharp knife-like cutting edge 42 completely therearound defining the opening 17a into passage 17. Hook 40 is of a dagger-like shape and has a sharp pointed end 58. The outer face of the hook tapers inwardly and the inner face is generally flat and parallel to the cutting edge 42. Hook 40 extends completely across the diameter of the opening 17a and its pointed end extends across the point of the cutting edge 42. As shown, only a relatively small portion of the area of opening 17a is obscured by the hook. It should be understood that the shape of the hook 40 can be selected as desired to obscure more or less of opening 17a.

In operation, the inner and outer members are moved longitudinally apart to provide a space between the inner face of hook 40 and the cutting edge 42. The instrument is moved to place the material to be cut between the two. For example, the hook 40 is slipped over the top of the object. The suction flow through passage 17 aids somewhat in properly positioning the portion of the object to be severed. Movement of outer member 18 towards inner member 16 causes a firm engagement to be made with the material between the inner face of the hook and the cutting edge. Further movement of the two members toward each other will cause a combined crushing and cutting action as the material is drawn against cutting edge 42. The material cut loose from the object is drawn into the opening 17a by the suction pressure, through the suction passage 17 of larger cross-section of the inner member and out to the collection spot. The two members are then moved apart to be again positioned to sever additional material from the object.

The combined crushing and cutting action is capable of severing pieces of relatively hard material from a larger object. That is, the hook 40 draws the material against the cutting edge with a controlled, but relatively large, amount of force. Further, the use of the hook 40 prevents the material from slipping away from the cutting edge 42.

The combined crushing and cutting action is carried out as many times as is necessary to remove the desired amount of material. Motor 34 can be operated at slow speed to move the two members together to perform the severing action and at a fast speed to move them apart.

As indicated previously, members 16 and 18 are preferably also made rotatable relative to each other. In FIG. 2, rotation is achieved by rotating the cap 21. In addition to the longitudinal reciprocating action between the two members which draws the material against the cutting edge 42, rotating the two members relative to each other enhances the cutting action.

FIGS. 4A and 4B show a further embodiment of the active front end of the instrument of the invention where the knife-shaped cutting edge 59 of the inner member 16 is serrated. The remainder of the instrument is as previously described. The points of the serrations 59 lie in the same plane which is here also shown generally parallel to the flat inner face of the hook 60. The hook 60 here is broader than hook 40 of FIG. 3 to provide a firmer grip of the material to be cut. In this case, the hook 60 obscures a larger portion of the opening 17a.

The instrument of FIGS. 4A–4B operates as described previously. The serrated cutting edge 59 and broader hook 60 provides a different type of cutting action than that of FIGS. 3A–3B since the serrations 59 will pierce into the object.

The active end of the instrument shown in FIG. 5 is particularly useful to dig into an object to be severed in that the hook end 70 extends inwardly toward passage 17. The remainder of the instrument and its operation is as previously described.

Figure 5B:
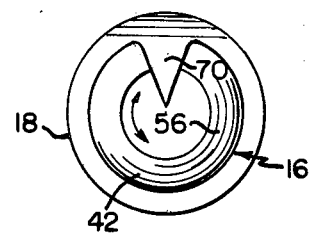

FIGS. 5A–5B show further embodiment of the active front end in which the cutting edge 42 of the inner member 16 is the same as that shown in FIG. 3. Here, a hook 70 is provided which is bent back inwardly toward the inner member. The hook 70 is relatively sharp and its pointed end terminates short of the central portion of the passage 17. In this embodiment the inner and outer members can be rotated relative to each other since the cutting edge 42 is generally flat.

Figure 6A:
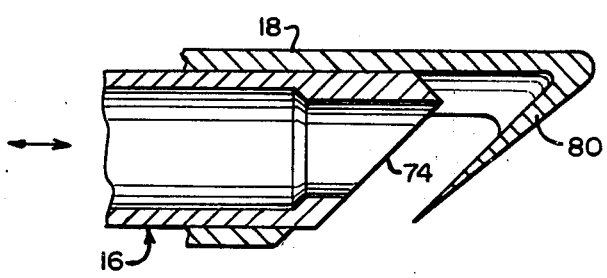
Figure 6B:
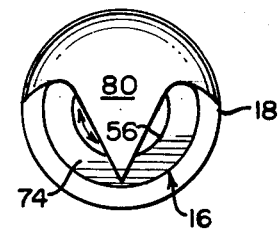

FIGS. 6A-6B show a further embodiment of the active front end of the instrument. Here, the forward end of the inner member 16 is cut off at an angle to form a forward cutting surface 74. The hook member 80 is bent inwardly and, in this case, extends completely across the front opening 56 to form a hood. A large part of the opening 17a is obscured.

The embodiment of FIGS. 6A-6B is also useful for piercing and digging into an abject. Here, due to the angled cutting face 74 and angled hook 80, only a limited amount of rotation is available between the two members. The cutting action of this embodiment is quite good since the hook extends across the opening 17a and the inner face of the hook is parallel to the cutting edge 74. The remainder of the instrument is as previously described.

Figure 7A:
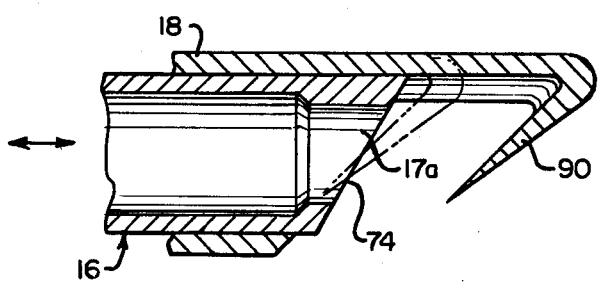
Figure 7B:
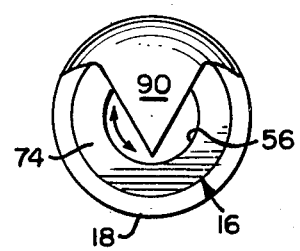

FIGS. 7A-7B show a modification of the active front end of FIGS. 6A-6B. Here, the hook 90 is bent inwardly parallel to the angled cutting face 74 and its end terminates short of extending completely across the opening 17a. In this case, the hook 90 can be retracted to within the passage 17 as shown by the dotted line in FIG. 7A. In this case, a limited amount of rotation is possible between the two members.

Figure 8A:
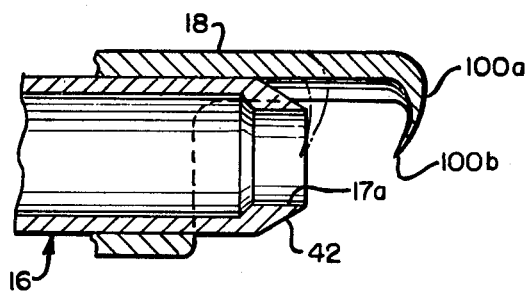
Figure 8B:
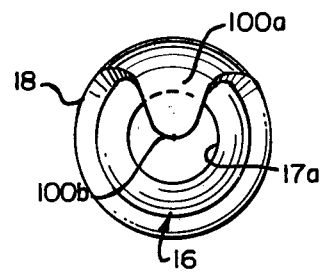

FIGS. 8A-8B show another embodiment of the active front end which is similar to that of FIGS. 5-5A. Here, the hook is curved over and its terminal end 100a is substantially on the central axis line of the coaxial tubular members. The end 100b of the hook terminal is above the diametrical center line of the inner member 16. Therefore, it extends into opening 17a. The curved hook provides good gripping action for the material being cut to move it against the cutting surface 42. There, after being severed, it is drawn into the suction passage 17.

FIGS. 9A-9B show an active front end with a rotatable cusp type of cutter 110. The inner tubular member 16 has a jaw 112 at its end which is generally scooped out, or concave, terminating in an arcuate pointed front end member 113 which is canted inwardly toward the passage 117. The edges 114 on each side of the jaws and on the front member 113 are sharpened. The outer tubular member 18 also has a scooped out jaw 122 with an inwardly angled front end 123. Jaw 122 has two points, or cusps, 124 and 125 on each side thereof. The rear cusp 124 is about one half to two-thirds of the way back on the length of the jaw 122. The front cusp 125 is at the front end of jaw 122. The edge around the jaw 122 is sharpened to provide a cutting surface.

As seen in FIGS. 9A and 9B the two jaws 112 and 122 are not symmetrical. The front of its left-hand edge (see in FIG. 9B) of the lower jaw 112 is higher than the front of the right-hand edge. Also jaw 112, fits within jaw 122. During operation, jaws 112 and 122 are rotated relative to each other. This is accomplished with the instrument of FIG. 2 by fixedly attaching the end of shaft 16a to the collar 34a and removing the set screw 16c so that rotation can be accomplished by the motor. As an alternate to this, cap 21 can be rotated.

As the jaws 112 and 114 are rotated relative to each other, material to be severed comes between them. There is a shearing action of the material by the edges of the jaws. The cusps 124 on jaw 122 provide a digging or crunching action.

FIG. 10 shows a further embodiment of the invention wherein the outer member 18 carries a jaw 130 thereon which is similar in some respects to jaw 122 of FIG. 9. Here, however, the end of the jaw tapers over into a hook 132 which terminates at or slightly above the central axis of the instrument. The lower jaw 140 on the inner member 16 has a single cusp 142 on one edge thereof and terminates in an upwardly extending hook 144. The other side 145 of the lower jaw is formed substantially arcuately. The entire lower jaw 140 will turn within the upper jaw 130. Upper jaw 130 has a cusp 143 on each side and a hooked end 132.

Both jaws 130 and 140 are hollow and generally concave. By rotating the two jaws with respect to each other, the object to be cut can be hooked by either members 132 or 144. The cusps 124 and 143 provide a side gripping and crunching action.

While the surgical instrument has been described with respect to a gripping and cutting action, it shall be understood that it can be used for gripping purposes only, that is, a foreign body can be gripped between the scoop and the cutting edge. Bodies of a semi-solid character often can be gripped more readily when the scoop has a portion, such as 100b of FIG. 8, for example, which can dig into the body.

What is claimed is:

1. A surgical instrument for crushing and severing material from an object comprising:
   first and second elongated members, one of said members being tubular with an open end and having a cutting surface formed at least partially around said open end thereof,
   said first and second members being telescopically mounted relative to each other,
   the other of said members having a gripping implement thereon which is shaped with a hook having an end which terminates in an acute angle for gripping the material of the object, the face of said gripping implement opposing said cutting surface having a portion which opposes and overlies a portion of said cutting surface so that the two can be brought into an abutting relationship without moving said gripping implement into the open end of said one member,
   means for moving said first and second members longitudinally relative to each other so that the gripping element moves the material against the cutting surface to crush the material against said cutting surface and to sever it with at least a part of the severed material being moved into said open end of said one member.

2. A surgical instrument as in claim 1 wherein the cutting surface is formed fully around said one open end of said one member.

3. A surgical instrument as in claim 2 wherein said one end of said one member is generally cylindrical and said cutting surface is formed completely therearound.

4. A surgical instrument as in claim 1 wherein said cutting surface is serrated.

5. A surgical instrument as in claim 1 wherein said one end of said one member having the cutting surface thereon is formed at an angle of less than 90° with respect to the longitudinal axis of said one member.

6. A surgical instrument as in claim 1 wherein the inner face of the implement opposing the cutting surface is generally parallel to the cutting surface.

7. A surgical instrument as in claim 1 further comprising means for rotating said cutting surface relative to said implement.

8. A surgical instrument as in claim 1 wherein said one end of said one tubular member is open and further comprising means for applying suction pressure through the member having the open end to draw the severed material into said tubular member.

9. A surgical instrument as in claim 8 wherein there is a passage formed between said first and second members and an opening formed in the outer member in communication with said passage, further comprising means for supplying irrigation fluid to said passage to exit through said opening.

10. A surgical instrument as in claim 1 further comprising means for supplying irrigation fluid through a portion of said instrument.

11. A surgical instrument as in claim 5 wherein said implement is hook shaped with an end that terminates in an acute angle and extends across the open end of said one member.

12. A surgical instrument as in claim 5 wherein said implement is hook shaped with the pointed end of the implement hook entering the open end of said one member.

13. A surgical instrument for crushing and severing material from an object comprising:
 first and second elongated members, one of said members having an open end and having a cutting surface formed at least partially around said open end thereof,
 the other of said members having a hook shaped gripping implement thereon for gripping the material of the object,
 said first and second members being tubular and coaxially and telescopically mounted relative to each other with the other member on the outside so that said implement extends forwardly of said one member,
 the face of said gripping implement opposing said cutting surface having a portion which at least partially overlies said cutting surface but always leaving a part of the open end of said one member open, and
 means for moving said first and second members longitudinally relative to each other so that the gripping element moves the material against the cutting surface to crush the material against said cutting surface and to sever it with at least a part of the severed material being moved into said open end of said one member.

14. A surgical instrument as in claim 13 wherein said hook shaped implement has a generally dagger-like shape with a pointed end.

15. A surgical instrument as in claim 13 wherein the face of said implement opposing the cutting surface and said cutting surface are both generally transverse to the longitudinal axes of said elongated members.

16. A surgical instrument as in claim 13 wherein the inner face of the implement opposing the cutting surface is generally parallel thereto with both said inner face and said cutting surface being at an angle of less than 90° with respect to the longitudinal axes of such members.

17. A surgical instrument as in claim 13 wherein said implement extends across the open end of said one member.

18. A surgical instrument as in claim 13 wherein the end of the hook shaped implement terminates in the open end of said one member.

19. A surgical instrument as in claim 18 wherein said hook shaped implement is bent inwardly to extend into the open end of said one member.

20. A surgical instrument for crushing and severing material from an object comprising:
 first and second elonated members, one of said members being tubular with an open end and having a cutting surface formed at least partially around said open end thereof at an angle of less than 90° with respect to the longitudinal axis of said one member,
 said first and second members being telescopically mounted relative to each other,
 the other of said members having a gripping implement thereon for gripping the material of the object, the face of said gripping implement opposing said cutting surface being generally parallel to said cutting surface and having a portion which overlies a portion of said cutting surface,
 means for moving said first and second members longitudinally relative to each other so that the gripping element moves the material against the cutting surface to crush the material against said cutting surface and to sever it with at least a part of the severed material being moved into said open end of said one member.

* * * * *